United States Patent [19]

Quarroz

[11] Patent Number: 4,681,942

[45] Date of Patent: Jul. 21, 1987

[54] PROCESS FOR THE PRODUCTION OF 3,5-DICHLORO-2-PYRIDONE

[75] Inventor: Daniel Quarroz, Canton Valais, Switzerland

[73] Assignee: Lonza Ltd., Gampel/Valais, Switzerland

[21] Appl. No.: 875,927

[22] Filed: Jun. 19, 1986

[30] Foreign Application Priority Data

Jun. 25, 1985 [CH] Switzerland ............... 2691/85

[51] Int. Cl.[4] .................................. C07D 211/72
[52] U.S. Cl. .................... 546/303; 546/345
[58] Field of Search .......................... 546/303

[56] References Cited

U.S. PATENT DOCUMENTS 4,287,347 9/1981 Fäh et al. ............... 546/345

FOREIGN PATENT DOCUMENTS 194823 6/1967 U.S.S.R. .

OTHER PUBLICATIONS

Cava and Bhattacharyya, Journal of Organic Chemistry 23, 1614 (1958).
Sutter and Weis, Journal of Heterocyclic Chemistry 17, 493 (1980).

*Primary Examiner*—Henry R. Jiles
*Assistant Examiner*—Zinna Northington
*Attorney, Agent, or Firm*—Fisher, Christen & Sabol

[57] ABSTRACT

3,5-Dichloro-2-pyridone is produced by chlorination starting from 6-hydroxynicotinic acid.

9 Claims, No Drawings

PROCESS FOR THE PRODUCTION OF 3,5-DICHLORO-2-PYRIDONE

BACKGROUND OF THE INVENTION

1. Field Of The Invention

The invention relates to a new process for the production of 3,5-dichloro-2-pyridone, which, on its part, can easily be converted to 2,3,5-trichloropyridine.

2. Prior Art 2,3,5-Trichloropyridine forms an educt in great demand for the production of a wide range of insecticides [P. Sutter et al., J.Het.Chem. 17, 493 (1980)].

The production of 3,5-dichloro-2-pyridone in a yield of 63 percent by chlorination, starting from 2-pyridone is known [Cava et al., J. Org. Chem. 23, 1614 (1958)]. According to U.S.S.R. Pat. No 194,823 (Appl. 4/20/1966), it is also known to obtain 3,5-dichloro-2-pyridone in mixture with 5-chloropyridone starting from 2-pyridone by reaction with tert-butyl hypochlorite.

But these known processes have the drawback that, in each case, it is necessary to start with relatively expensive 2-pyridone.

BROAD DESCRIPTION OF THE INVENTION

The object of the invention is to provide a process which makes it possible to produce the desired 3,5-dichloro-2-pyridone, starting from a favorable educt, in a simple way and in good yield and quality.

The object of the invention is achieved according to the invention process wherein 6-hydroxynicotinic acid is reacted with chlorine or chlorine-releasing agents, whereby the product is 3,5-dichloro-2-pyridone having the formula:

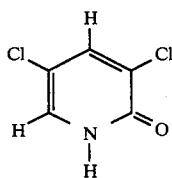

The hypochlorites, especially the alkali or alkaline earth metal hypochlorites, are suitable chlorine-releasing agents. Sodium or potassium hypochlorite is particularly suitable and preferred. The hypochlorite, dissolved in water, is advantageously added in a concentration of 5 to 25 percent, preferably 8 to 14 percent.

The chlorination agents are generally added in an excess in relation to the stoichiometric ratio. In the case of hypochlorites, the excess is advantageously from 0 to 300 percent, preferably from 20 to 50 percent. If chlorine is used, the excess is advantageously from 0 to 300 percent, preferably from 20 to 50 percent.

Advantageously, the process is performed in the presence of water as a solvent.

A suitable reaction temperature is advantageously between 0° and 40° C., preferably between 0° and 20° C.

Moreover, care is taken so that the pH range is between 7 and 12, preferably between 8 and 11, if a hypochlorite or chlorine is used as the chlorination agent.

After the halogenation is completed, the 3,5dichloro-2-pyridone can be removed from the reaction solution in any suitable, simple way, e.g., by filtering or extraction. The yields are generally over 70 percent.

Optionally, the product can be purified by recrystallization, e.g., in water, ethyl acetate or toluene. But, usually the quality of the raw product is adequate for further conversion to 2,3,5-trichloropyridine, e.g., according to the process of U.S. Pat. No. 4,287,347 (the pertinent parts of which are incorporated herein by reference).

2,3,5-trichloropyridine can be produced by reacting 3,5-dichloro-2-pyridone at 30° to 150° C. with phosgene in the presence of an N,N-disubstituted formamide of the formula:

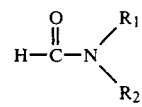

in which $R_1$ and $R_2$ can be identical or different and are each an alkyl group having 1 to 4 carbon atoms, or $R_1$ and $R_2$ together with the nitrogen atom form the pyrrolidino, piperidino or morpholino, and in the presence of an inert solvent. 2,3,5-trichloropyridine is an intermediate for producing herbicidally active α-[4-(3′,5′-dichloropyrid-2-yloxy)-phenoxy]-alkanecarboxylic acids and derivates thereof.

DETAILED DESCRIPTION OF THE INVENTION

As used herein, all parts, percentages, ratios and proportions are on a weight basis unless otherwise stated herein or otherwise obvious herein to one skilled in the art.

EXAMPLE 1

70 g (0.5 mol) of 6-hydroxynicotinic acid was suspended in 500 ml of water and then brought into solution (pH of the solution was 10) with sodium hydroxide solution. 100 g of chlorine was slowly introduced at 0° C. The pH was kept between 10 and 11 by the addition of NaOH. The chlorination ended after 2 hours. The resultant slightly yellow precipitate was filtered off by suction at pH 5, washed with water and then dried under vacuum at 50° C. 63.5 g (77.4 percent yield) of 3,5-dichloro-2-pyridone was obtained.

1H-NMR (CDCl3): (ppm); 7.5 (d); 7.72 (d).

EXAMPLE 2

8.3 g (0.06 mol) of 6-hydroxynicotinic acid was suspended in 30 ml of water and then brought into solution (pH of solution was 8) with sodium hydroxide solution. 76.5 g of a 13.6 percent solution of NaOCl in water was slowly added at 5° C. During the addition, the pH was kept between 7 and 8.5. When the reaction was ended, the resultant slightly yellow precipitate was filtered off by suction, washed with water and then dried under vacuum at 50° C. 7.0 g (71.1 percent yield) of 3,5-dichloro-2-pyridone was obtained.

1H-NMR (CDCl3): (ppm); 7.5 (d); 7.72

What is claimed is:

1. Process for the production of 3,5-dichloro2-pyridone having the formula:

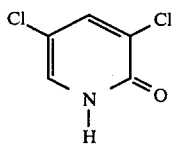

comprising reacting 6-hydroxynicotinic acid with chlorine or a chlorine-releasing agent.

2. Process as claimed in claim 1 wherein the chlorine-releasing agent is an alkali metal hypochlorite or an alkaline earth metal hypochlorite.

3. Process as claimed in claim 2 wherein the chlorine-releasing agent is sodium hypochlorite or potassium hypochlorite.

4. Process as claimed in claim 3 wherein the reaction is conducted in the presence of water as a solvent.

5. Process as claimed in claim 4 wherein the reaction is conducted at a pH of 7 to 12.

6. Process as claimed in claim 5 wherein the reaction is conducted at a temperature of 0° to +40° C.

7. Process as claimed in claim 1 wherein the reaction is conducted in the presence of water as a solvent.

8. Process as claimed in claim 1 wherein the reaction is conducted at a pH of 7 to 12.

9. Process as claimed in claim 1 wherein the reaction is conducted at a temperature of 0° to +40° C.

* * * * *